(12) United States Patent
Blanz

(10) Patent No.: US 7,825,661 B2
(45) Date of Patent: Nov. 2, 2010

(54) METHOD AND APPARATUS FOR NMR SATURATION

(75) Inventor: Martin Blanz, Celle (DE)

(73) Assignee: Baker Hughes Incorporated, Houston, TX (US)

( * ) Notice: Subject to any disclaimer, the term of this patent is extended or adjusted under 35 U.S.C. 154(b) by 27 days.

(21) Appl. No.: 12/200,479

(22) Filed: Aug. 28, 2008

(65) Prior Publication Data

US 2009/0058416 A1  Mar. 5, 2009

Related U.S. Application Data

(60) Provisional application No. 60/969,501, filed on Aug. 31, 2007, provisional application No. 60/978,954, filed on Oct. 10, 2007.

(51) Int. Cl.
*G01V 3/00* (2006.01)
(52) U.S. Cl. .................................. 324/307
(58) Field of Classification Search ......... 324/300–322; 600/410–435
See application file for complete search history.

(56) References Cited

U.S. PATENT DOCUMENTS

| | | | | |
|---|---|---|---|---|
| 5,023,551 | A * | 6/1991 | Kleinberg et al. | 324/303 |
| 5,486,762 | A * | 1/1996 | Freedman et al. | 324/303 |
| 5,680,043 | A * | 10/1997 | Hurlimann et al. | 324/303 |
| 6,215,304 | B1 | 4/2001 | Slade | |
| 6,242,913 | B1 | 6/2001 | Prammer | |
| 6,331,775 | B1 | 12/2001 | Thern et al. | |
| 6,492,809 | B1 * | 12/2002 | Speier et al. | 324/303 |
| 6,531,868 | B2 | 3/2003 | Prammer | |
| 6,566,874 | B1 * | 5/2003 | Speier et al. | 324/303 |
| 6,703,832 | B2 * | 3/2004 | Heaton et al. | 324/303 |
| 6,844,728 | B2 * | 1/2005 | Speier et al. | 324/303 |
| 6,859,033 | B2 * | 2/2005 | Speier | 324/303 |
| 6,952,096 | B2 * | 10/2005 | Freedman | 324/303 |
| 6,956,371 | B2 * | 10/2005 | Prammer | 324/303 |
| 7,164,267 | B2 * | 1/2007 | Prammer et al. | 324/303 |
| 7,196,516 | B2 * | 3/2007 | Blanz et al. | 324/303 |
| 7,358,725 | B2 * | 4/2008 | Blanz | 324/303 |
| 7,372,264 | B2 * | 5/2008 | Akkurt et al. | 324/303 |
| 7,564,240 | B2 * | 7/2009 | Ganesan | 324/303 |
| 7,622,919 | B2 * | 11/2009 | Song et al. | 324/307 |

FOREIGN PATENT DOCUMENTS

| EP | 0837338 A2 | 4/1998 |
|---|---|---|
| GB | 2346216 A | 8/2000 |

OTHER PUBLICATIONS

Dietrich et al., "Neues Verfahren zur Bestimmung der longitudinalen Relaxationszeit in der Kernresonanzspektroskopie,I" Z. Anal. Chem. 279, 1976, pp. 177-181.

* cited by examiner

*Primary Examiner*—Brij B Shrivastav
*Assistant Examiner*—Dixomara Vargas
(74) *Attorney, Agent, or Firm*—Mossman Kumar & Tyler PC

(57) ABSTRACT

Saturation pulse sequences are designed to ensure complete saturation of nuclear spins for dual wait time measurements and saturation recovery measurements in the case of axial motion of a downhole NMR logging tool. Frequency and/or phase modulation may be used. An auxiliary saturation coil may be used.

19 Claims, 13 Drawing Sheets ic field at a
METHOD AND APPARATUS FOR NMR SATURATION

CROSS-REFERENCES TO RELATED APPLICATIONS

This application claims priority from U.S. Provisional Patent Application Ser. No. 60/969,501 filed on Aug. 31, 2007 and from U.S. Provisional Patent Application Ser. No. 60/978,954 filed on Oct. 10, 2007.

BACKGROUND OF THE DISCLOSURE

1. Field of the Disclosure

The present disclosure relates generally to determining geological properties of subsurface formations using Nuclear Magnetic Resonance ("NMR") methods for logging wellbores, particularly the use of saturation pulse sequences in the presence of axial tool motion for dual wait time and $T_1$ saturation recovery measurements.

2. Description of the Related Art

A variety of techniques are utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, the tools designed to provide the desired information are used to log the wellbore. Much of the logging is done after the well bores have been drilled. More recently, wellbores have been logged while drilling, which is referred to as measurement-while-drilling (MWD) or logging-while-drilling (LWD).

One recently evolving technique involves utilizing Nuclear Magnetic Resonance (NMR) logging tools and methods for determining, among other things, porosity, hydrocarbon saturation and permeability of the rock formations. The NMR logging tools are utilized to excite the nuclei of the liquids in the geological formations surrounding the wellbore so that certain parameters such as spin density, longitudinal relaxation time (generally referred to in the art as $T_1$) and transverse relaxation time (generally referred to as $T_2$) of the geological formations can be measured. From such measurements, porosity, permeability and hydrocarbon saturation are determined, which provides valuable information about the make-up of the geological formations and the amount of extractable hydrocarbons.

The NMR tools generate a uniform or near uniform static magnetic field in a region of interest surrounding the wellbore. NMR is based on the fact that the nuclei of many elements have angular momentum (spin) and a magnetic moment. The nuclei have a characteristic Larmor resonant frequency related to the magnitude of the magnetic field in their locality. Over time the nuclear spins align themselves along an externally applied magnetic field. This equilibrium situation can be disturbed by a pulse of an oscillating magnetic field, which tips the spins with resonant frequency within the bandwidth of the oscillating magnetic field away from the static field direction. The angle θ through which the spins exactly on resonance are tipped is given by the equation:

$$\theta = \gamma B_1 t_p \quad (1),$$

where γ is the gyromagnetic ratio, $B_1$ is the effective field strength of the oscillating field and $t_p$ is the duration of the RF pulse.

After tipping, the spins precess around the static field at a particular frequency known as the Larmor frequency $\omega_0$, given by $$\omega_o = \gamma B_0 \quad (2)$$

where $B_0$ is the static field intensity. At the same time, the spins return to the equilibrium direction (i.e., aligned with the static field) according to an exponential decay time known as the spin-lattice relaxation time or $T_1$. For hydrogen nuclei, $\gamma/2\pi = 4258$ Hz/Gauss, so that a static field of 235 Gauss would produce a precession frequency of 1 MHz. $T_1$ of fluid in pores is controlled totally by the molecular environment and is typically ten to one thousand milliseconds in rocks.

At the end of a θ=90° tipping pulse, spins on resonance are pointed in a common direction perpendicular to the static field, and they precess at the Larmor frequency. However, because of inhomogeneities in the static field due to the constraints on tool shape, imperfect instrumentation, or microscopic material heterogeneities, each nuclear spin precesses at a slightly different rate. Hence, after a time long compared to the precession period, but shorter than $T_1$, the spins will no longer be precessing in phase. This de-phasing occurs with a time constant that is commonly referred to as $T_2^*$ if it is predominantly due to the static field inhomogeneity of the apparatus, and as $T_2$ if it is due to properties of the material.

The receiving coil is designed so that a voltage is induced by the precessing spins. Only that component of the nuclear magnetization that is precessing in the plane perpendicular to the static field is sensed by the coil. After a 180° tipping pulse (or an "inversion pulse"), the spins on resonance are aligned opposite to the static field and the "precession" consists of a slow return along the static field axis to the equilibrium direction. Hence, a signal will be generated after a 90° tipping pulse, but not after a 180° tipping pulse in a generally uniform magnetic field.

Saturation in NMR means "destroying all magnetization". Saturation is needed within Dual Wait Time (DTW) and $T_1$ saturation recovery measurements. In the field of NMR the term $T_1$ is called the longitudinal relaxation time while the term $T_2$ is the transverse relaxation time. The DTW comprises two NMR echo trains, one starting with full magnetization after a long wait time TW (e.g. 6 s or more), the other starting after a shorter wait time of e.g. TW=1 s. If the NMR echoes of the two sequences are different then this is caused by formation components with $T_1$>approx. 0.5 s. The DTW method, therefore, provides some information about $T_1$. For the method to work it is important that for the sequence with TW=1 s, this sequence starts with zero magnetization, also called saturation. See, for example, U.S. Pat. No. 6,331,775 to Thern et al., having the same assignee as the present disclosure and the contents of which are incorporated herein by reference. An aperiodic saturation sequence (APS) works well where the logging tool is stationary (W. Dietrich et. al, Z. Anal. Chem. 279, 177-181 (1976)). If, on the other hand, the logging tool moves between the application of the saturation sequence and the following NMR echo sequence, then the saturated region is not coincident with the region where the NMR echoes come from. As a consequence, the saturation is not effective, and DTW measurements give wrong answers.

The use of wide-band saturation pulses that are relatively insensitive to lateral tool motion has been discussed in prior art. Not addressed in prior art is the issue of movement of the logging tool along the borehole axis. This can be a problem for a rate of penetration (ROP) greater than 20 m/h, depending upon the configuration of the logging tool. It should be noted that all the examples and discussions herein are specific to the NMR tool described in FIG. 2. With more elaborate wideband saturation sequences, the problem can be overcome and effective saturation becomes possible even in excess of ROP=100 m/h.

SUMMARY OF THE DISCLOSURE

One embodiment of the disclosure is an apparatus for evaluating an earth formation. The apparatus includes a downhole assembly configured to be conveyed in a borehole; a magnet arrangement on a tool on the downhole assembly configured to generate a static magnetic field in the earth formation; at least one radio-frequency (RF) coil on the downhole assembly configured to generate an RF field in the earth formation; and a processor configured to activate the at least one RF coil with a first pulse sequence which substantially saturates nuclear spins in a region of the earth formation, activate the at least one RF coil with a second pulse sequence that generates at least one signal from the region of substantial saturation and generates substantially no signal form outside the region, wherein there is an axial movement of the tool between a start time of the first pulse sequence and an end time of the second pulse sequence.

Another embodiment of the disclosure is a method of evaluating an earth formation. The method includes conveying a downhole assembly in a borehole; using a magnet arrangement on a tool on the downhole assembly to generate a static magnetic field in a region of the earth formation; using at least one radio-frequency (RF) coil to generate an RF field in the earth formation; and activating the at least one RF coil with a first pulse sequence which substantially saturates nuclear spins in the region and with a second pulse sequence that generates at least one signal from the region of substantial saturation of spins and generates no signal from outside the region, wherein there is an axial movement of the tool between a start time of the first pulse sequence and an end time of the second pulse sequence.

Another embodiment of the disclosure is a computer-readable medium accessible to a processor. The medium includes instructions which enable the processor to determine a property of an earth formation selected from (I) a longitudinal relaxation time $T_1$ of the formation, (II) a transverse relaxation time $T_2$ of the formation, and (III) a fluid content of the formation using at least one signal from an earth formation acquired by a nuclear magnetic resonance tool following application of: a static magnetic field in the earth formation during an axial motion of the tool, a first radio frequency (RF) pulse sequence which substantially saturates nuclear spins in a region of the earth formation, and a second pulse sequence that generates the at least one signal from the region, wherein the second pulse sequence generates substantially no signal from outside the region.

BRIEF DESCRIPTION OF THE DRAWINGS

The present disclosure is best understood with reference to the accompanying figures in which like numerals refer to like elements and in which.

DETAILED DESCRIPTION OF THE DISCLOSURE

Figure 1:
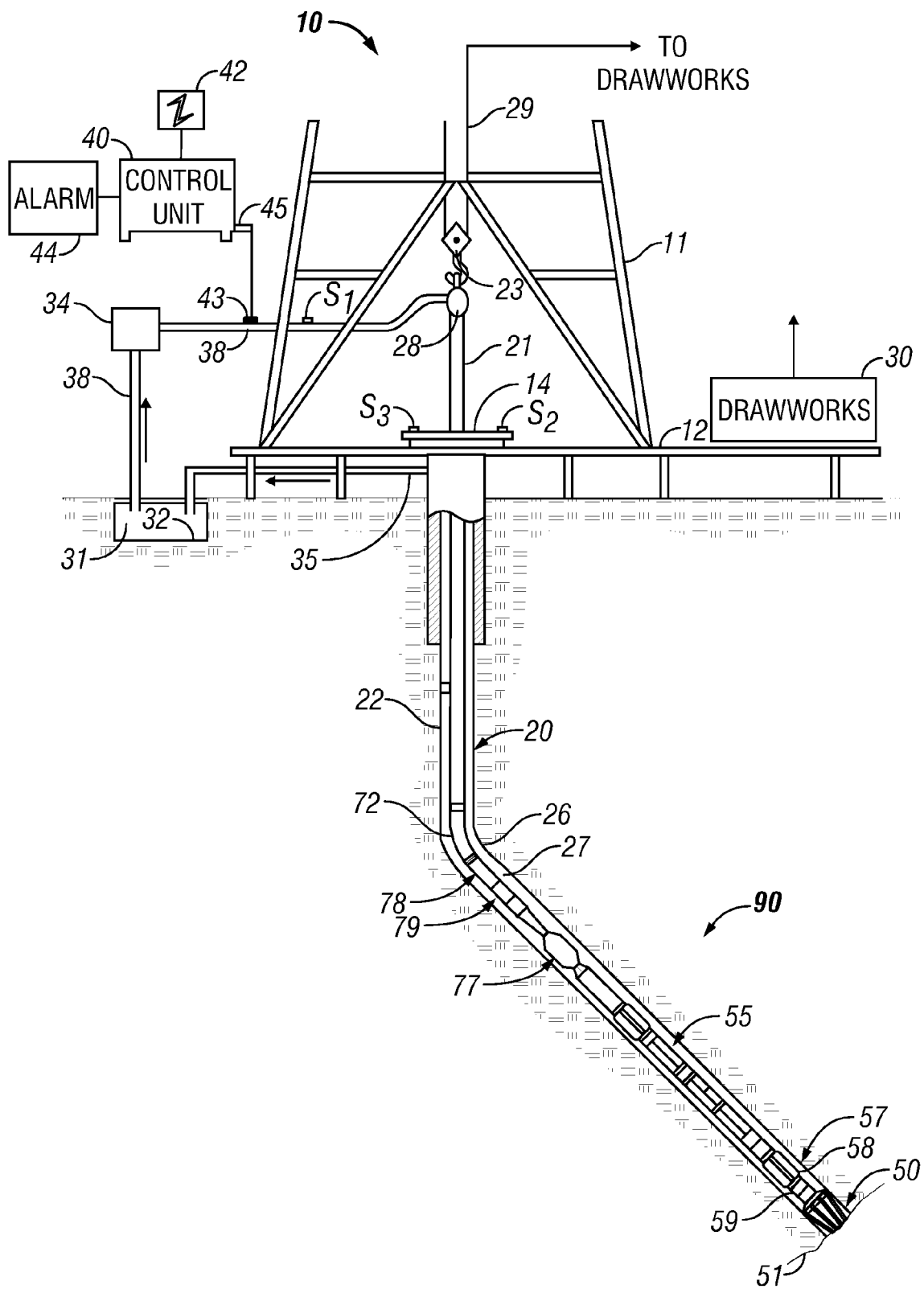
FIG. 1 (Prior Art) shows a measurement-while-drilling tool suitable for use with the present disclosure.

FIG. 1 shows a schematic diagram of a drilling system 10 with a drillstring 20 carrying a drilling assembly 90 (also referred to as the bottomhole assembly, or "BHA") conveyed in a "wellbore" or "borehole" 26 for drilling the wellbore. The drilling system 10 includes a conventional derrick 11 erected on a floor 12 which supports a rotary table 14 that is rotated by a prime mover such as an electric motor (not shown) at a desired rotational speed. The drillstring 20 includes a tubing such as a drill pipe 22 or a coiled-tubing extending downward from the surface into the borehole 26. The drillstring 20 is pushed into the wellbore 26 when a drill pipe 22 is used as the tubing. For coiled-tubing applications, a tubing injector, such as an injector (not shown), however, is used to move the tubing from a source thereof, such as a reel (not shown), to the wellbore 26. The drill bit 50 attached to the end of the drillstring breaks up the geological formations when it is rotated to drill the borehole 26. If a drill pipe 22 is used, the drillstring 20 is coupled to a drawworks 30 via a Kelly joint 21, swivel 28, and line 29 through a pulley 23. During drilling operations, the drawworks 30 is operated to control the weight on bit, which is an important parameter that affects the rate of penetration. The operation of the drawworks is well known in the art and is thus not described in detail herein. During drilling operations, a suitable drilling fluid 31 from a mud pit (source) 32 is circulated under pressure through a channel in the drillstring 20 by a mud pump 34. The drilling fluid passes from the mud pump 34 into the drillstring 20 via a desurger (not shown), fluid line 38 and Kelly joint 21. The drilling fluid 31 is discharged at the borehole bottom 51 through an opening in the drill bit 50. The drilling fluid 31 circulates uphole through the annular space 27 between the drillstring 20 and the borehole 26 and returns to the mud pit 32 via a return line 35. The drilling fluid acts to lubricate the drill bit 50 and to carry borehole cutting or chips away from the drill bit 50. A sensor $S_1$ typically placed in the line 38 provides information about the fluid flow rate. A surface torque sensor $S_2$ and a sensor $S_3$ associated with the drillstring 20 respectively provide information about the torque and rotational speed of the drillstring. Additionally, a sensor (not shown) associated with line 29 is used to provide the hook load of the drillstring 20.

In one embodiment of the disclosure, the drill bit 50 is rotated by only rotating the drill pipe 22. In another embodiment of the disclosure, a downhole motor 55 (mud motor) is disposed in the drilling assembly 90 to rotate the drill bit 50 and the drill pipe 22 is rotated usually to supplement the rotational power, if required, and to effect changes in the drilling direction.

In an exemplary embodiment of FIG. 1, the mud motor 55 is coupled to the drill bit 50 via a drive shaft (not shown) disposed in a bearing assembly 57. The mud motor rotates the drill bit 50 when the drilling fluid 31 passes through the mud motor 55 under pressure. The bearing assembly 57 supports the radial and axial forces of the drill bit. A stabilizer 58 coupled to the bearing assembly 57 acts as a centralizer for the lowermost portion of the mud motor assembly.

In one embodiment of the disclosure, a drilling sensor module 59 is placed near the drill bit 50. The drilling sensor module contains sensors, circuitry and processing software and algorithms relating to the dynamic drilling parameters. Such parameters typically include bit bounce, stick-slip of the drilling assembly, backward rotation, torque, shocks, borehole and annulus pressure, acceleration measurements and other measurements of the drill bit condition. A suitable telemetry or communication sub 72 using, for example, two-way telemetry, is also provided as illustrated in the drilling assembly 90. The drilling sensor module processes the sensor information and transmits it to the surface control unit 40 via the telemetry system 72.

The communication sub 72, a power unit 78 and an MWD tool 79 are all connected in tandem with the drillstring 20. Flex subs, for example, are used in connecting the MWD tool 79 in the drilling assembly 90. Such subs and tools form the bottom hole drilling assembly 90 between the drillstring 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface. Alternatively, the signals can be processed using a downhole processor in the drilling assembly 90.

The surface control unit or processor 40 also receives signals from other downhole sensors and devices and signals from sensors $S_1$-$S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 typically includes a computer or a microprocessor-based processing system, memory for storing programs or models and data, a recorder for recording data, and other peripherals. The control unit 40 is typically adapted to activate alarms 44 when certain unsafe or undesirable operating conditions occur.

A suitable device for use of the present disclosure is disclosed in U.S. Pat. No. 6,215,304 to Slade, the contents of which are fully incorporated herein by reference. It should be noted that the device taught by Slade is for exemplary purposes only, and the method of the present disclosure may be used with many other NMR logging devices, and may be used for wireline as well as MWD applications.

Figure 2:
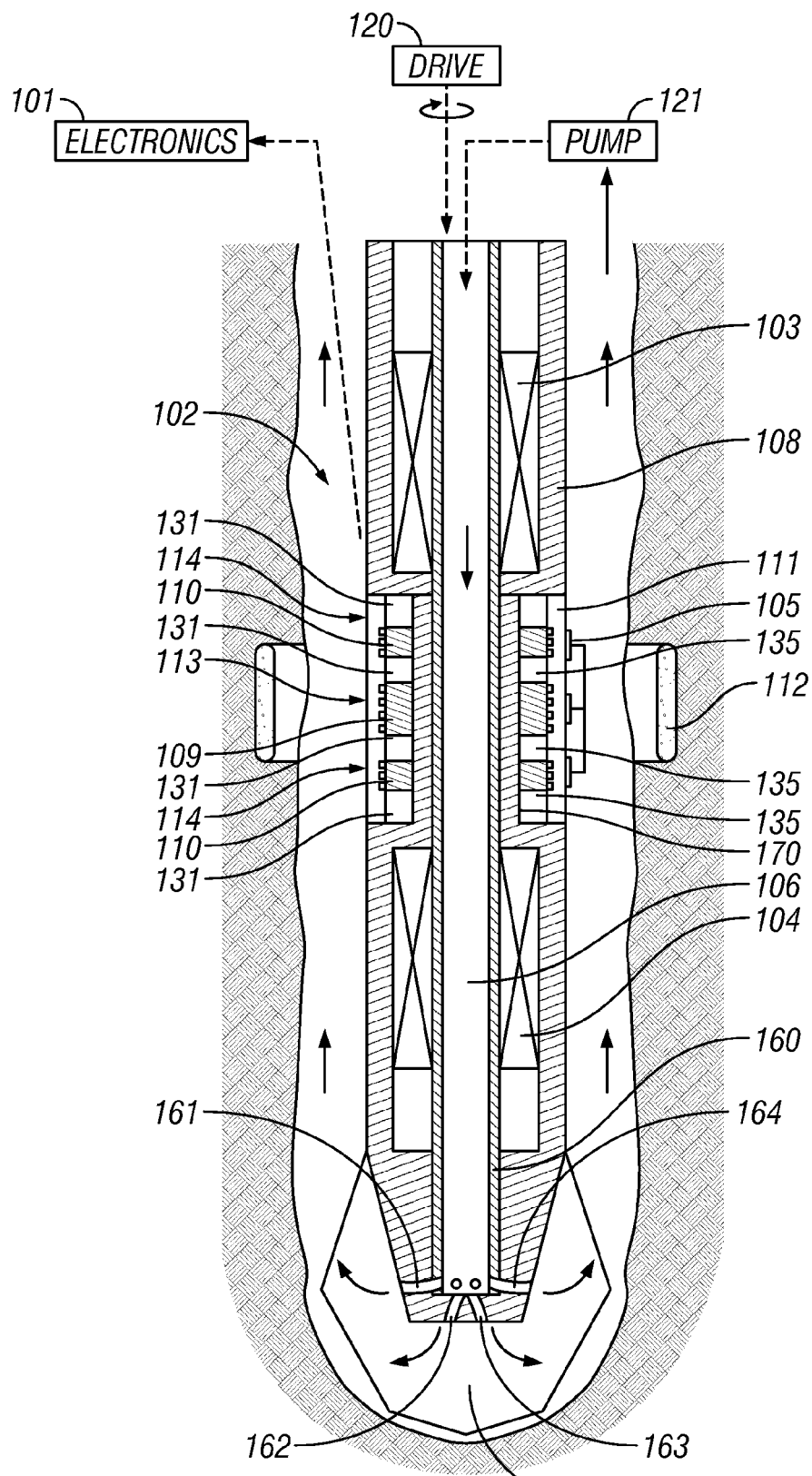
FIG. 2 (Prior Art) shows a sensor section of a measurement-while-drilling device suitable for use with the present disclosure.

Referring now to FIG. 2, the tool has a drill bit 107 at one end, a sensor section 102 behind the drill head, and electronics 101. The sensor section 102 comprises a magnetic field generating assembly for generating a $B_0$ magnetic field (which is substantially time invariant over the duration of a measurement), and an RF system for transmitting and receiving RF magnetic pulses and echoes. The magnetic field generating assembly comprises a pair of axially spaced main magnets 103, 104 having opposed pole orientations (i.e. with like magnetic poles facing each other), and three ferrite members 109, 110 axially arranged between the magnets 103, 104. The ferrite members are made of "soft" ferrite which can be distinguished over "hard" ferrite by the shape of the BH curve which affects both intrinsic coercivity ($H_j$ the intersection with the H axis) and initial permeability ($\mu_i$, the gradient of the BH curve in the unmagnetized case). Soft ferrite $\mu_i$ values typically range from 10 to 10000 whereas hard ferrite has $\mu_i$, of about 1. Therefore the soft ferrite has large initial permeability (typically greater than 10, preferably greater than 1000). The RF system comprises a set of RF transmit antenna and RF receive antenna coil windings 105 arranged as a central "field forming" solenoid group 113 and a pair of outer "coupling control" solenoid groups 114. This is shown in more detail in FIG. 16.

Figure 16:
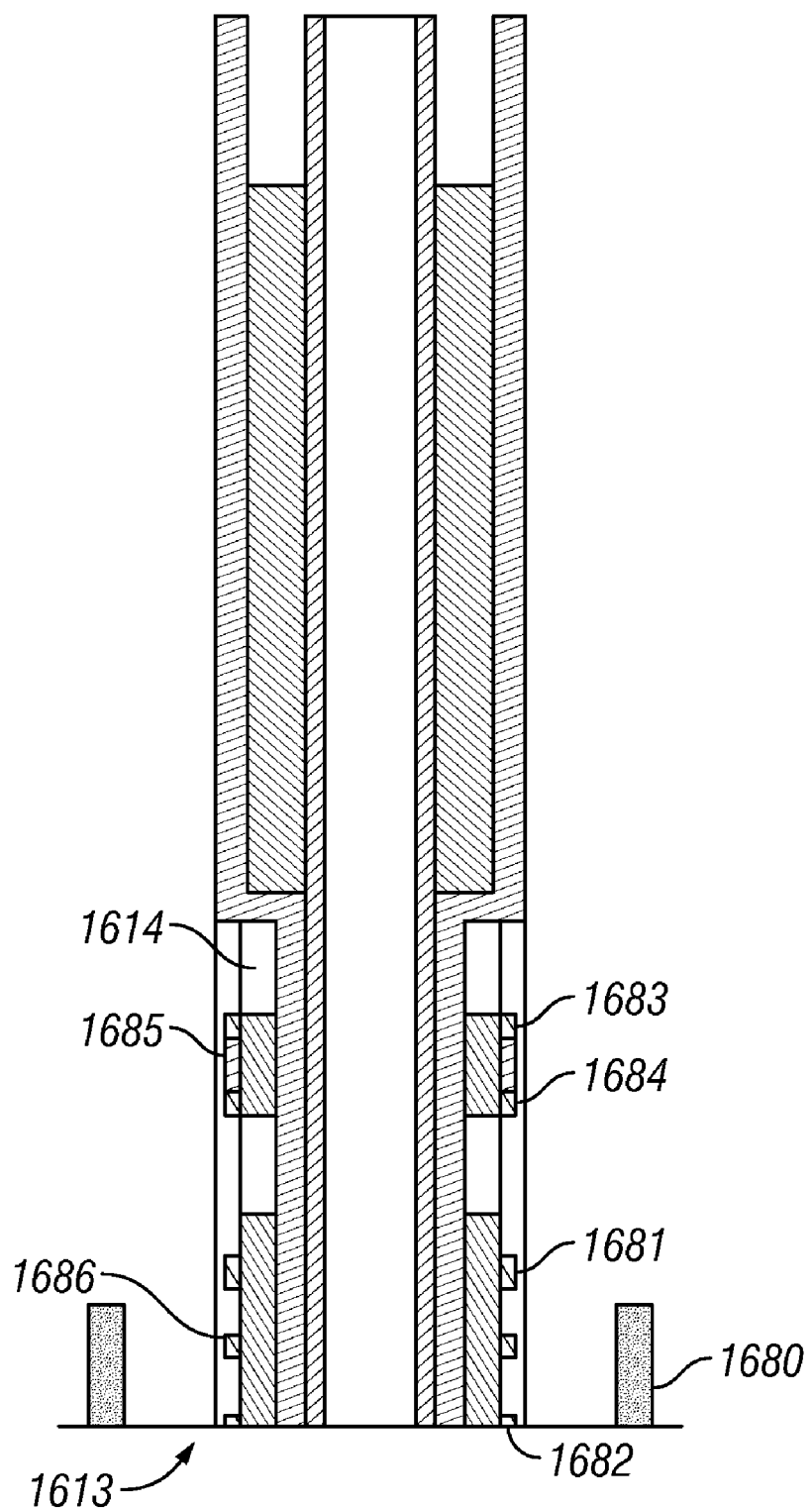
FIG. 16 shows a detail of the transmitter and receiver coil arrangement for one embodiment of the disclosure.

As discussed in Slade, the central "field forming" solenoid group 1613 comprises three positively wound transmit coil winding groups and two receive coil winding groups all wound in the same sense. Each winding group comprises a number of solenoidal turns. FIG. 16 shows one of the two outer transmit coil winding groups 1681 (the other being located on the opposite side of centre plane 1680), half of the central transmit coil winding group 1682 (the other half being located on the opposite side of centre plane 1680), and one of the two receive coil winding groups 1686 (the other being located on the opposite side of centre plane 1680).

Each "coupling control" solenoid group 1614 comprises a pair of receive coil winding groups 1683, 1684 wound in the same sense as the field forming winding groups and a transmit coil winding group 1685 wound in the opposite sense. All coils in both groups allocated to the transmit coil are series connected as are all those allocated to the receive coil. The coil and number of turns positions are selected to produce substantially uniform axially oriented RF flux across the sensitive volume, thus creating conditions for NMR, whilst simultaneously cancelling the mutual inductance of the transmit and receive coils. The system of "zero-coupling coils" is described in EP-A-0837338 of Slade. Furthermore, as also described in Slade '388, the design of the twin RF coil system is such that it does not generate any NMR signal within the borehole region (for example, from vestigial borehole lobes). Consequently, the present disclosure does not require the use of gradient coils to cancel the borehole signal. The importance of having three transmit coils in the central "field forming group" will be discussed below.

The tool has a mud pipe 160 with a clear central bore 106 and a number of exit apertures 161-164 to carry drilling mud to the bit 107, and the main body of the tool is provided by a drill collar 108. Drilling mud is pumped down the mud pipe 160 by a pump 121 returning around the tool and the entire tool is rotated by a drive 120. Coiled tubing or a drillstring may be used for coupling the drive to the downhole assembly.

The drill collar 108 provides a recess 170 for RF transmit antenna and RF receive antenna coil windings 105. Gaps in the pockets between the soft ferrite members are filled with non-conducting material 131, 135 (e.g.: ceramic or high temperature plastic) and the RF coils 113, 114 are then wound over the soft ferrite members 109, 110. The soft ferrites 109, 110 and RF coil assembly 113, 114 are pressure impregnated with suitable high temperature, low viscosity epoxy resin (not shown) to harden the system against the effects of vibration, seal against drilling fluid at well pressure, and reduce the possibility of magnetoacoustic oscillations. The RF coils 113, 114 are then covered with wear plates 111 typically ceramic or other durable non-conducting material to protect them from the rock chippings flowing upwards past the tool in the borehole mud.

Because of the axisymmetric magnet configuration, the device of Slade has an axisymmetric magnetic field and region of investigation 112 that is unaffected by tool rotation. Use of the ferrite results in a region of investigation that is close to the borehole. This is not a major problem on a MWD tool because there is little invasion of the formation by borehole drilling fluids prior to the logging. The region of investigation is within a shell with a radial thickness of about 20 mm and an axial length of about 50 mm. The gradient within the region of investigation is less than 2.7 G/cm. It is to be noted that these values are for the Slade device and, as noted above, the method of the present disclosure may also be used with other suitable NMR devices.

Generally, the geometry of the NMR measurement device gives rise to a volume in the earth formation where the $B_0$ field has the correct strength to fulfill a resonance condition and in which an RF field can be presented with a substantial strength and orientation to reorient nuclear spins within the volume. This volume is often referred to as the sensitive volume. For a tool in motion, as the tool moves axially, the volume containing those protons excited by the excitation pulse (first pulse of the echo sequence) moves away from the sensitive volume. Hence, the number of spins available to contribute to the subsequent NMR signal is reduced with each subsequent echo. As a consequence, those echoes obtained later in an echo sequence with axial tool motion appear smaller compared to those echoes obtained later in an echo sequence acquired with no tool motion. "Later echoes" does not mean that only the last echoes of a sequence are affected. In fact, the loss of signal starts right at the beginning of a sequence and develops over time in a unique pattern.

The magnet configuration of FIG. 2 produces a somewhat inhomogeneous static magnetic $B_0$ field. Measured in the axial direction, this field has a minimum at the center of the NMR sensor and increases in magnitude to a maximum at the magnets. The result of this configuration on a volume of formation being traversed in an axial direction is that during constant axial motion the formation first comes close to one of the magnets and is magnetized by this higher field. As the NMR sensor center moves closer, the effective $B_0$ field decreases. But the formation "remembers" the earlier higher magnetization and only gradually decays, with the time constant $T_1$, towards the minimum equilibrium magnetization $B_0$ field located in the center.

The simplest possibility of NMR saturating is by a single 90° RF pulse. But any subsequent pulse will generate an NMR echo. In addition, the adjustment of the pulse length or height is critical. Considering that in the logging tool described above, the $B_1$ field is quite inhomogeneous, and $B_1$ is not everywhere orthogonal to $B_0$, it becomes obvious that a single 90° pulse is too simple. Historically, a train of pulses has been used with the idea in mind that whatever z magnetization is left by the previous pulse is turned into the xy plane by the following pulse and hence z magnetization is destroyed. For simplicity, equal wait times have been used between the pulses, i.e. a periodic pulse sequence. This works well for solid materials where the transverse relaxation time $T_2$ is usually orders of magnitude shorter than the longitudinal relaxation time $T_1$. There is a snag, though, with this method when applied to liquids with long $T_2$: By any two succeeding pulses an echo is created—just at the time where a third pulse is applied. As the third pulse is applied during the echo when the spins in the xy plane are focused, this pulse turns the xy magnetization into z. This is undesirable. Wolfgang Dietrich (Dietrich 1976) suggested an aperiodic sequence where the interpulse times form a geometric sequence of decreasing times.

An aperiodic saturation sequence (APS) of this kind was simulated for the logging tool of FIG. 2. The APS comprises eight RF pulses with reducing interpulse times 6400 μs, 3200 μs, 1600 μs, 800 μs, 400 μs, 200 μs, 100 μs. To increase the efficiency even more the phases are cycled as 0°, 180°, 90°, 270°, 0°, 180°, 90° and 270°. Hence the total duration of this sequence is 12.7 ms plus 8 times the length of the RF pulses.

Figure 3:
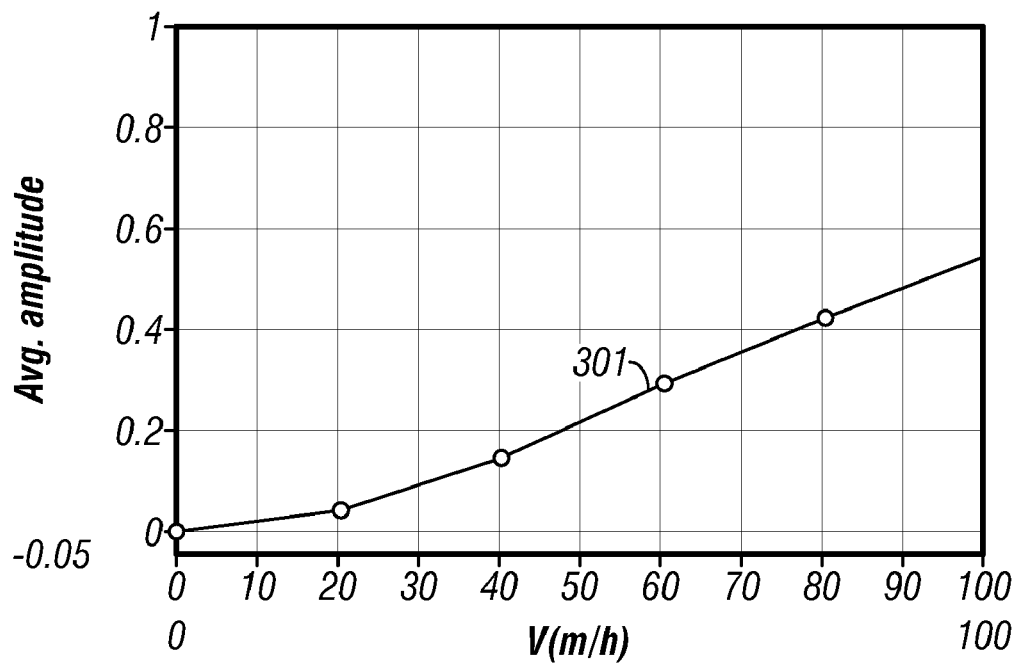
FIG. 3 shows the nuclear magnetization as a fraction of the equilibrium magnetization one second after an aperiodic saturation sequence.

This saturation sequence is effective when the logging tool is stationary, it becomes increasingly ineffective during fast drilling with high ROP. FIG. 3 shows the nuclear magnetization 301 as a fraction of the equilibrium magnetization 1 second after the aperiodic saturation sequence. The magnetization (ordinate) as a fraction of equilibrium magnetization is plotted against ROP (abscissa) in m/h. We see that for zero ROP, the saturation is perfect (magnetization is zero). For ROP of 100 m/h the saturation is inefficient and more than half of the equilibrium magnetization is left.

Figure 15:
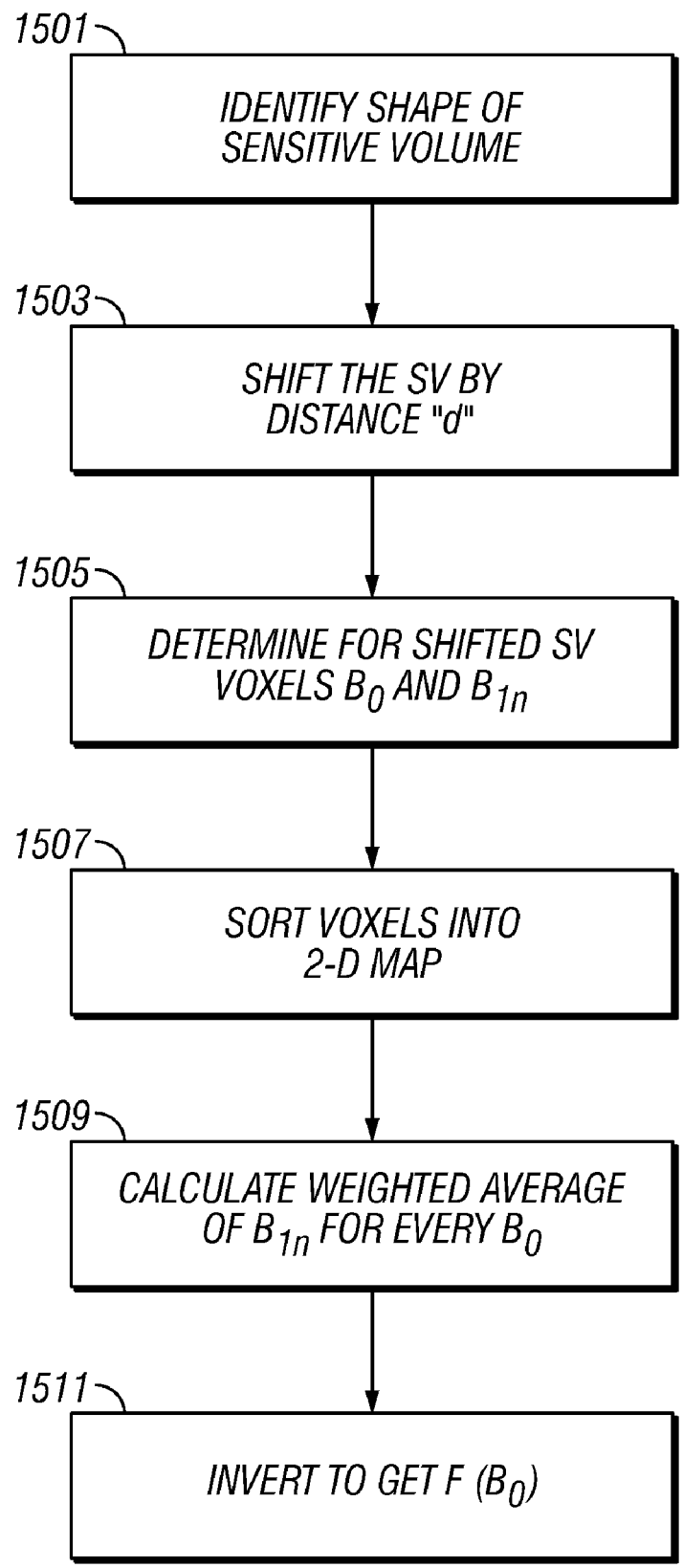
FIG. 15 shows a flow chart of methodologies that are used in designing the operational parameters of the tool.

An outflow effect is the reason why the saturation of FIG. 3 does not work well during axial movement. For example, at 100 m/h the tool moves about 30 mm within the wait time of 1 s, or otherwise expressed after 1 s the saturated region has moved by 30 mm relative to the NMR tool. The voxels saturated have to a large degree moved to regions with lower or higher $B_0$ field while new unsaturated formation has moved into the sensitive region. This new formation was not saturated because at the time when the saturation pulses were applied this formation was exposed to higher or lower $B_0$ field, outside the bandwidth of the saturation. The solution of the problem is therefore to use wide-band saturation. There are many different ways to achieve this and is discussed with reference to FIG. 15.

Figure 6:
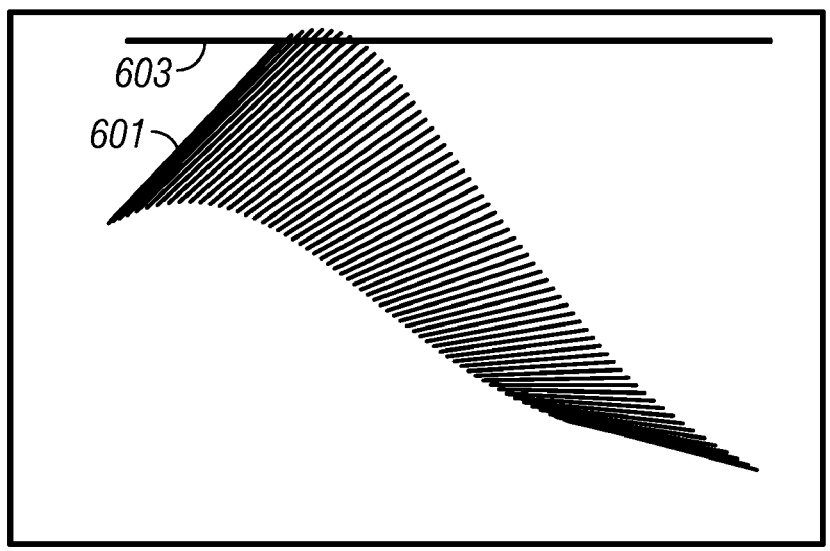
FIG. 6 shows voxels of the shifted sensitive volume of FIG. 4 sorted according to their $B_0$ field and $B_1$ field component that is orthogonal to $B_0$.

The shape of the sensitive NMR volume is determined 1501. This is the volume where $B_0$ is close to the resonant $B_0$. "Close" means within the equivalent bandwidth of RF pulses and NMR receiver. See FIG. 4 below for an example. Depending upon the wait time TW and max ROP, the SV in the magnetic field map is shifted 1503 by a distance "d" in the direction of movement. This is also illustrated above in FIG. 4. Next, for the shifted SV for all volume elements (voxels) $B_0$ and $B_{1n}$ are determined 1505, where $B_{1n}$ is the component of $B_1$ that is orthogonal to $B_0$. The voxels of the shifted sensitive volume are sorted into a 2-dimensional map 1507 of horizontal axis $B_0$ and vertical axis $B_{1n}$. This is illustrated in FIG. 6. A weighted average of $B_{1n}$ is calculated 1509 for every $B_0$, the weights being the $B_1$ components of the receiver coil that are orthogonal to $B_0$. The weights take care of the receiver coil sensitivity for a particular voxel of the SV. See for example FIG. 8. Let's call the resulting function $A(B_0)$. Next, $A(B_0)$ is inverted 1511 to get $f(B_0)=1/A(B_0)$, where $f(B_0)$ is the now the optimized frequency spectrum that we have to apply for saturation. For efficient NMR saturation, this frequency spectrum is applied with every RF pulse of the earlier described aperiodic pulse sequence (APS). This will saturate spins in a region that includes the original 1501 and shifted 1503 regions.

There are at least three ways to apply the frequency spectrum determined above for NMR saturation. These are:

A. Frequency modulation. This may be done with variable sweep rate and amplitude, variable sweep rate with constant amplitude, and fixed sweep rate with variable amplitude. All of these can be continuous or in discrete steps (applies to frequency and amplitude).

B. Phase modulation. This may be done with variable phase change rate and variable amplitude, sometimes referred to as complex amplitude modulation (for example to minimize power as described in U.S. Pat. No. 6,686,737 to Kruspe et al., having the same assignee as the present disclosure). This may also be done with variable phase change rate and constant amplitude. This may be done with a quadratic phase change rate and variable amplitude (discussed below). All of these can be continuous or in discrete steps (applies to phase and amplitude).

C. Other Methods, e.g. Stochastic Pulsing.

The use of stochastic pulsing (having a low power requirement) is discussed in U.S. Pat. No. 7,015,694 to Blumich having the same assignee as the present disclosure. Frequency sweeps and phase modulation can be designed to do exactly the same, the only difference being the implementation. It should further be noted that a broad band saturation using a $B_0$ sweep as discussed in U.S. Pat. No. 6,844,728 to Speier et al. is equivalent to a frequency sweep. Hence the methods discussed here of a tailor made frequency sweep are also applicable to saturation methods using a $B_0$ sweep. In the following embodiments, only methods that work with constant amplitude RF pulses are discussed.

Figure 4:
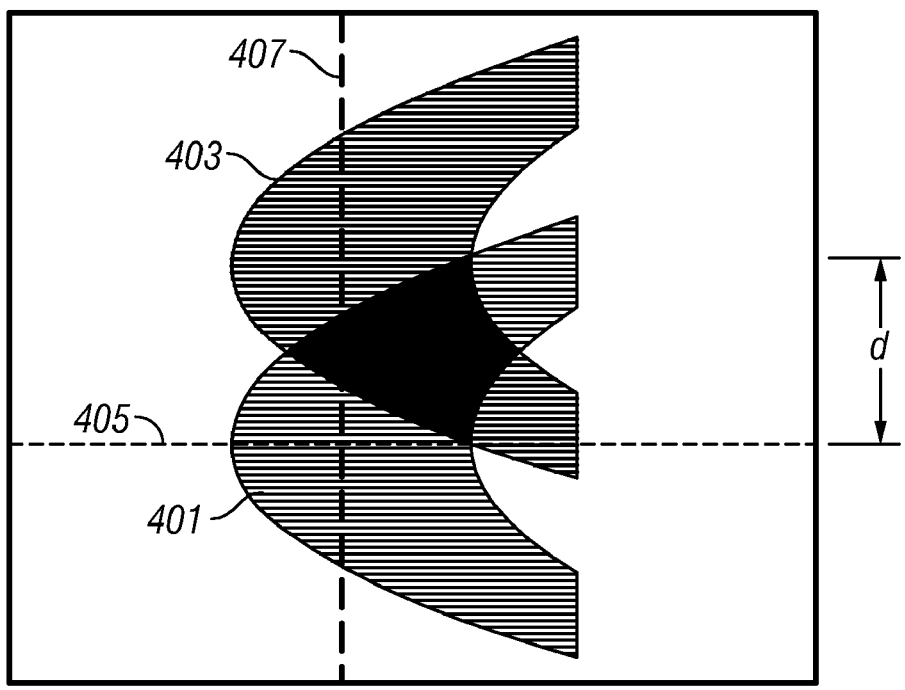
FIG. 4 shows the sensitive volume of the exemplary logging tool at two time instances with an axial displacement.

Turning to FIG. 4, the sensitive region of the NMR tool discussed above is shown by 401. The abscissa is distance from the borehole axis, and the ordinate is distance along the borehole axis. The sensitive region 403 corresponds to a displacement of the region 401 by a distance 'd'.

Figure 5:
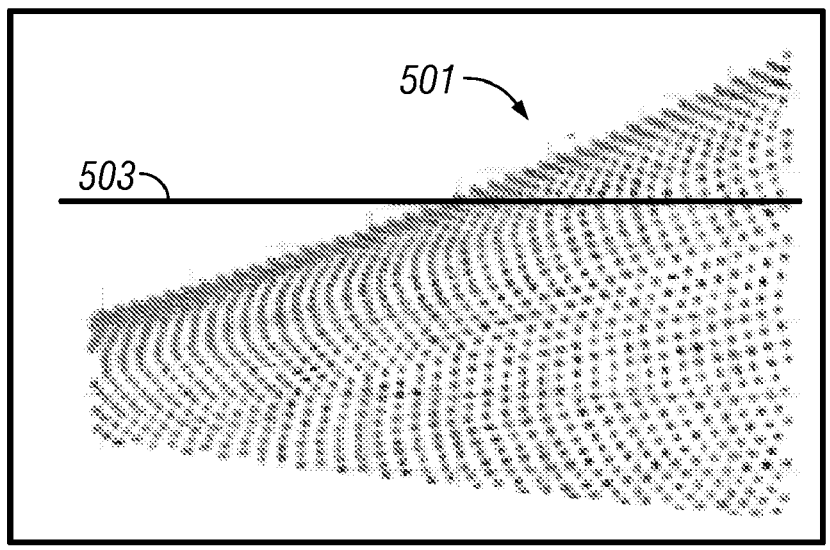
FIG. 5 shows the voxels of the sensitive volume of FIG. 4 sorted according to their $B_0$ field and $B_1$ field component that is orthogonal to $B_0$.
Figure 7:
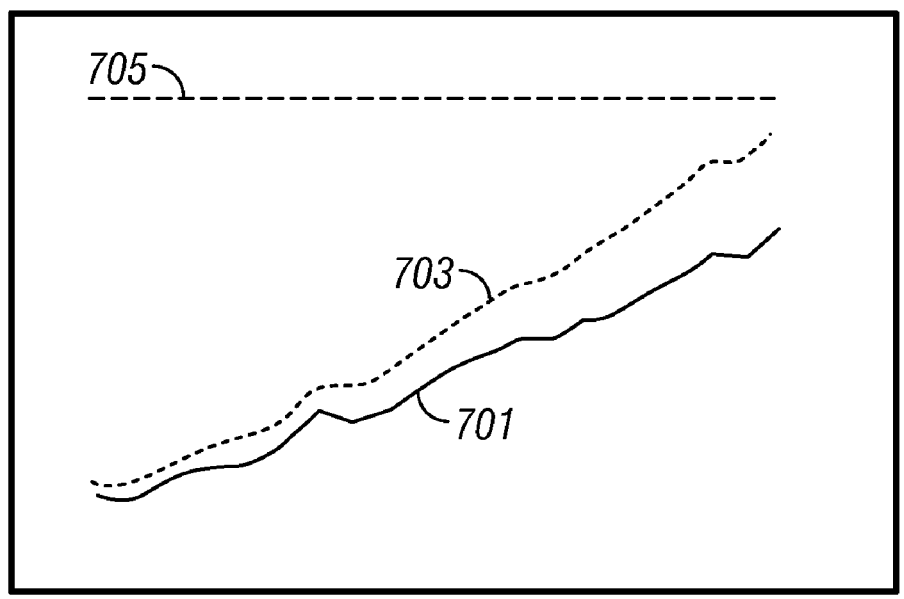
FIG. 7 shows the average $B_1$ component that is orthogonal to $B_0$ for each $B_0$ in FIG. 5.

For the efficiency of the RF pulse only the $B_1$ component that is orthogonal to $B_0$ is meaningful. FIG. 5 shows all the voxels 501 of the sensitive volume (401 in FIG. 4) now sorted according to their $B_0$ field and $B_1$ field component that is orthogonal to the $B_0$ field. The abscissa is the $B_0$ field in arbitrary units. Similarly, the ordinate is the $B_1$ component that is orthogonal to the $B_0$ field. The line 503 is the reference $B_1$ field at the nominal radius of the region of investigation and z=0 and is repeated as 603, 705 and 805 in FIGS. 6 to 8 respectively. FIG. 6 shows an equivalent plot of all the voxels 601 of the shifted sensitive volume, (403 in FIG. 4), now sorted according to their $B_1$ field component that is orthogonal to the $B_0$ field. 603 is the reference $B_1$ field. Next, shown in FIGS. 7-8 are average orthogonal $B_1$ values versus $B_0$ field. 701 is the simple average for the unshifted sensitive volume, 703 is a weighted average with weights proportional to the orthogonal $B_1$ component, and 705 is the reference $B_1$ value. 801 is the simple average for the shifted sensitive volume, 803 is a weighted average with weights proportional to the orthogonal $B_1$ component, and 805 is the reference $B_1$ value.

Figure 8:
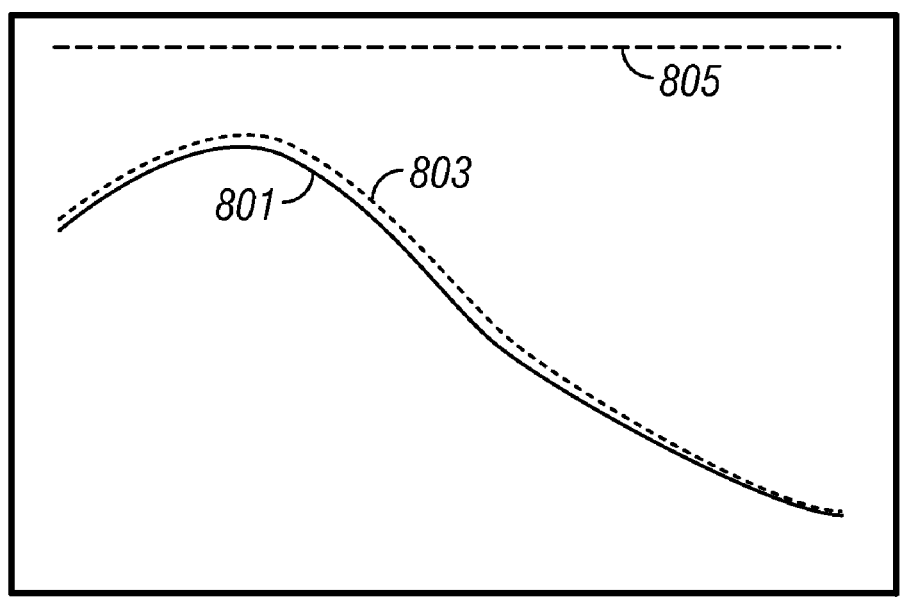
FIG. 8 shows the average $B_1$ component that is orthogonal to $B_1$ for each $B_0$ in FIG. 6.

FIG. 8 shows that the orthogonal $B_1$ average varies by a factor of 4 over the $B_0$ fields of the shifted sensitive volume. This means that for best saturation at the highest $B_0$ field (most right in the figure), the RF intensity must be 4 times of that at the peak of the curve. In one embodiment, pulses with constant amplitude are used. To vary the intensity of the frequency spectrum we can then choose the appropriate length of irradiation at each frequency. We must, however consider that the longer the irradiation at a specific frequency is, the smaller the bandwidth at that frequency will become. Hence, the longer the pulse components the closer the frequency spacing must be. One tailored example is shown by 901 in FIG. 9. The abscissa is time and the ordinate is frequency. FIG. 10 shows the frequency spectrum 1001 of the pulse 901. The abscissa is the frequency. 1003 shows for comparison the magnitude of the frequency distribution of a simple rectangular pulse at the nominal NMR frequency. The nominal NMR frequency is the NMR resonance frequency for a spot in the formation that is at the nominal radius at z=0.

For the simulation results below, it is assumed that $|B_1|$, or equivalently, the transmit current is independent of the frequency. This may not be true in a real NMR tool. Such an effect is not considered in the simulation but is easy to handle.

Figure 11:
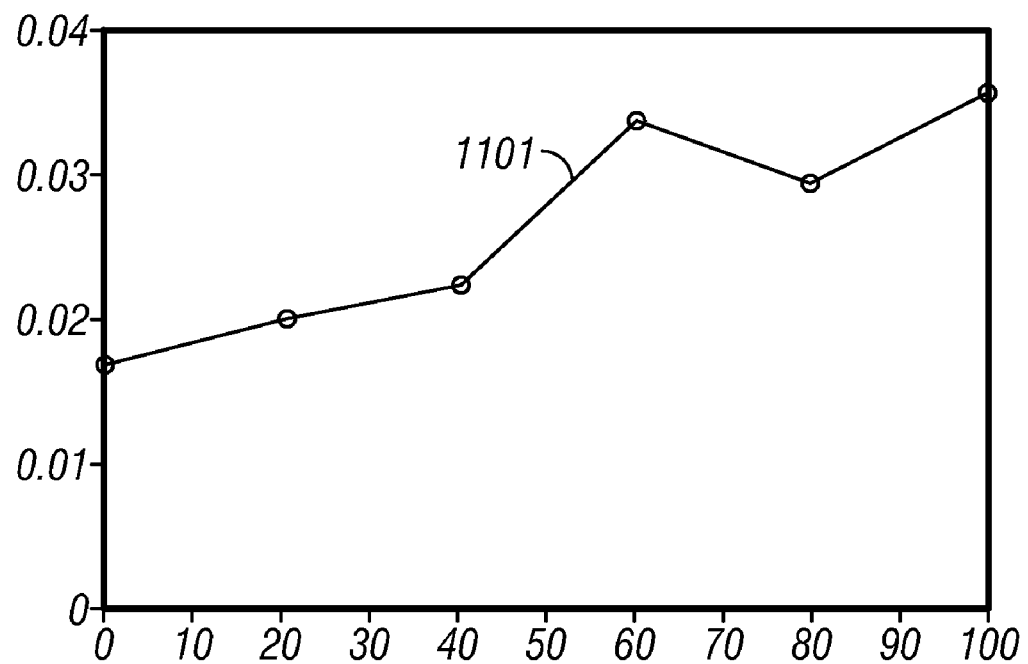
FIG. 11 shows the remaining magnetization after the variable frequency pulse.

Turning now to FIG. 11, simulation results are shown for the pulse 901. The curve 1101 is for the pulse 901 implemented as an aperiodic pulse sequence with phases of 0°, 180°, 90°, −90°, 0°, 180°, 90°, and −90°. We note that the residual magnetization after the tailored variable-frequency saturation with an aperiodic pulse sequence is less than 4% of total equilibrium, compared with about 55% in FIG. 3.

As an alternative to frequency modulation, phase modulation may be used. If continuous phase modulation is possible, a pulse can be generated that is completely equivalent to the frequency modulated pulse 901. We discuss here a specific implementation in which phase modulation is limited to steps of 90°. Even with this crude limitation, it is possible to construct a wideband pulse.

A phase modulated signal can be written as $\cos(\omega t + \phi(t))$. If the phase is constant, we get the signal $\cos(\omega t + \phi)$, a signal with constant angular frequency $\omega$. If the phase change is linear in time, then $\phi(t)=ct$, and we get the signal $\cos(\omega t + ct) = \cos(\omega + c)t$, i.e., a constant shift of the frequency by an amount c compared to the unmodulated signal. If the phase change is quadratic in time $\phi(t)=ct^2$, we get the signal $\cos(\omega + ct)t$, a signal with an offset frequency ct, of which the offset frequency is constantly increasing in time. This is a linear frequency sweep.

Figure 12A:
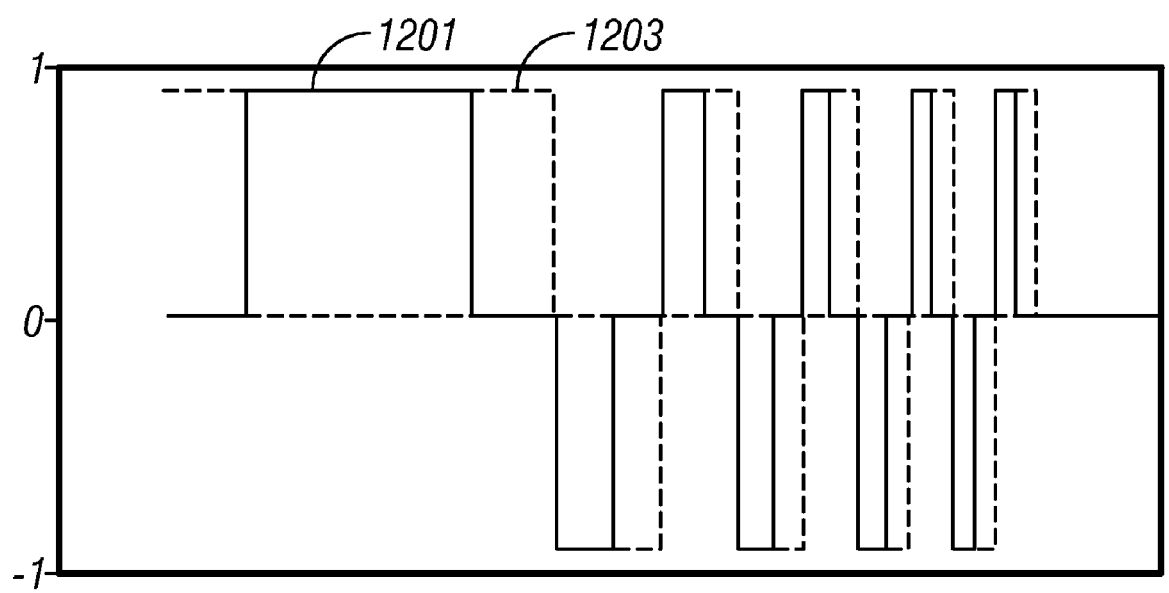
FIG. 12A shows quadratic phase modulation in discreet 90° steps as in-phase and quadrature signals.
Figure 12B:
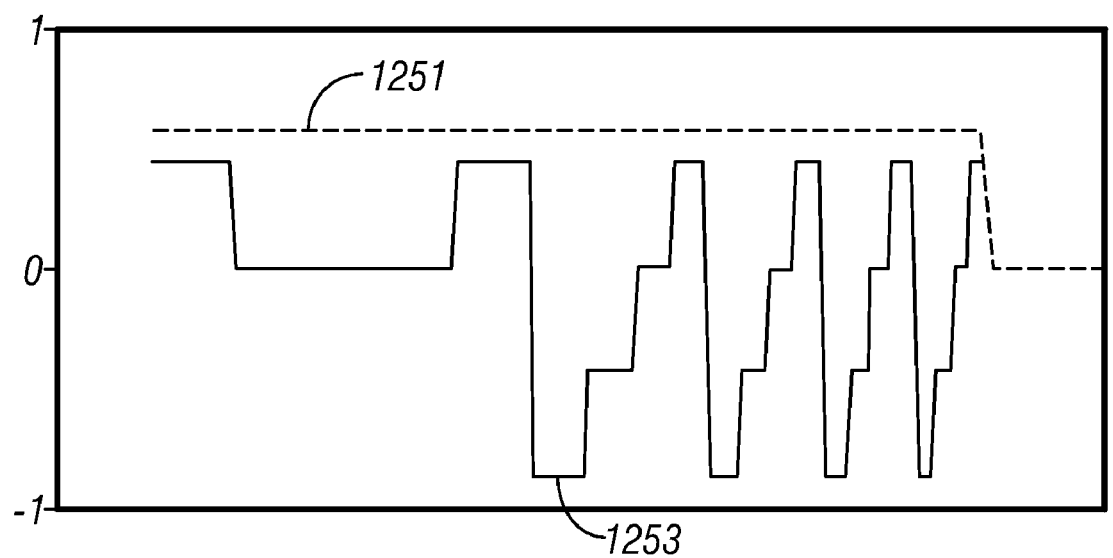
FIG. 12B shows quadratic phase modulation in discreet 90° steps as amplitude and phase.
Figure 13:
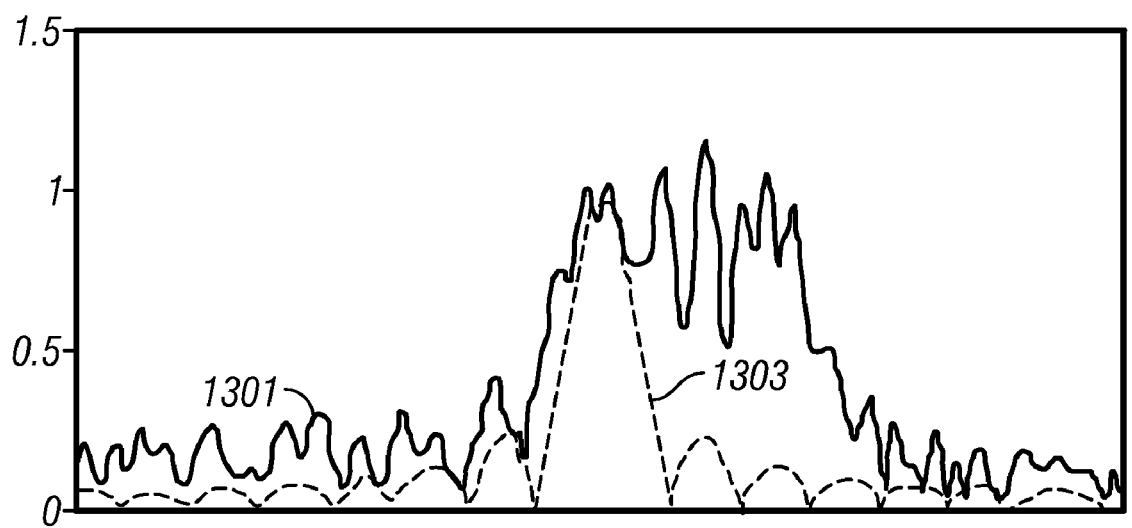
FIG. 13 shows the frequency spectra of the quadratic phase modulation and of a simple rectangular pulse.

Subject to the limitation of 90° step changes in phase, the implementation of an approximate quadratic phase change in time is shown in FIGS. 12A, 12B. 1201 and 1203 show the in-phase and quadrature signals, while 1251 and 1253 show the amplitude and phase respectively. The frequency spectrum is shown in FIG. 13 by the curve 1301 while 1303 is the spectrum of a rectangular pulse.

Figure 9:
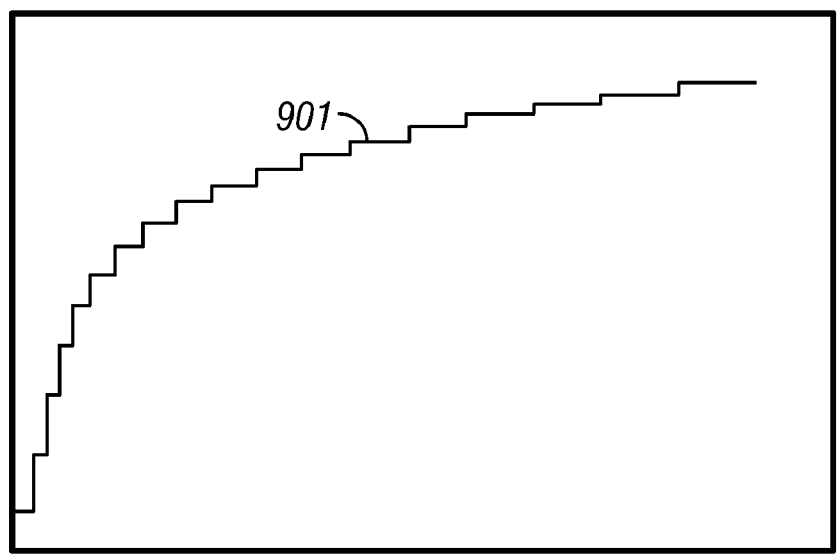
FIG. 9 shows a variable frequency pulse.
Figure 10:
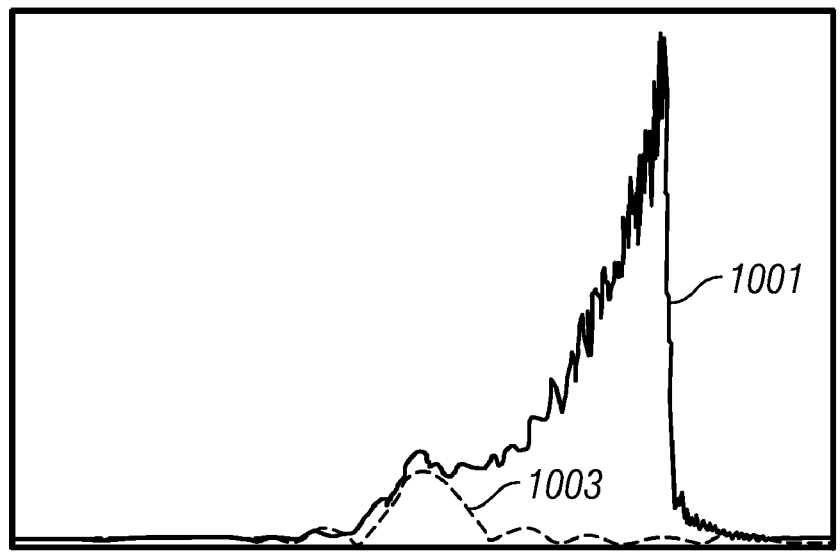
FIG. 10 shows the Fourier transform of the pulse of FIG. 9 and the frequency spectrum of a simple rectangular pulse.
Figure 14:
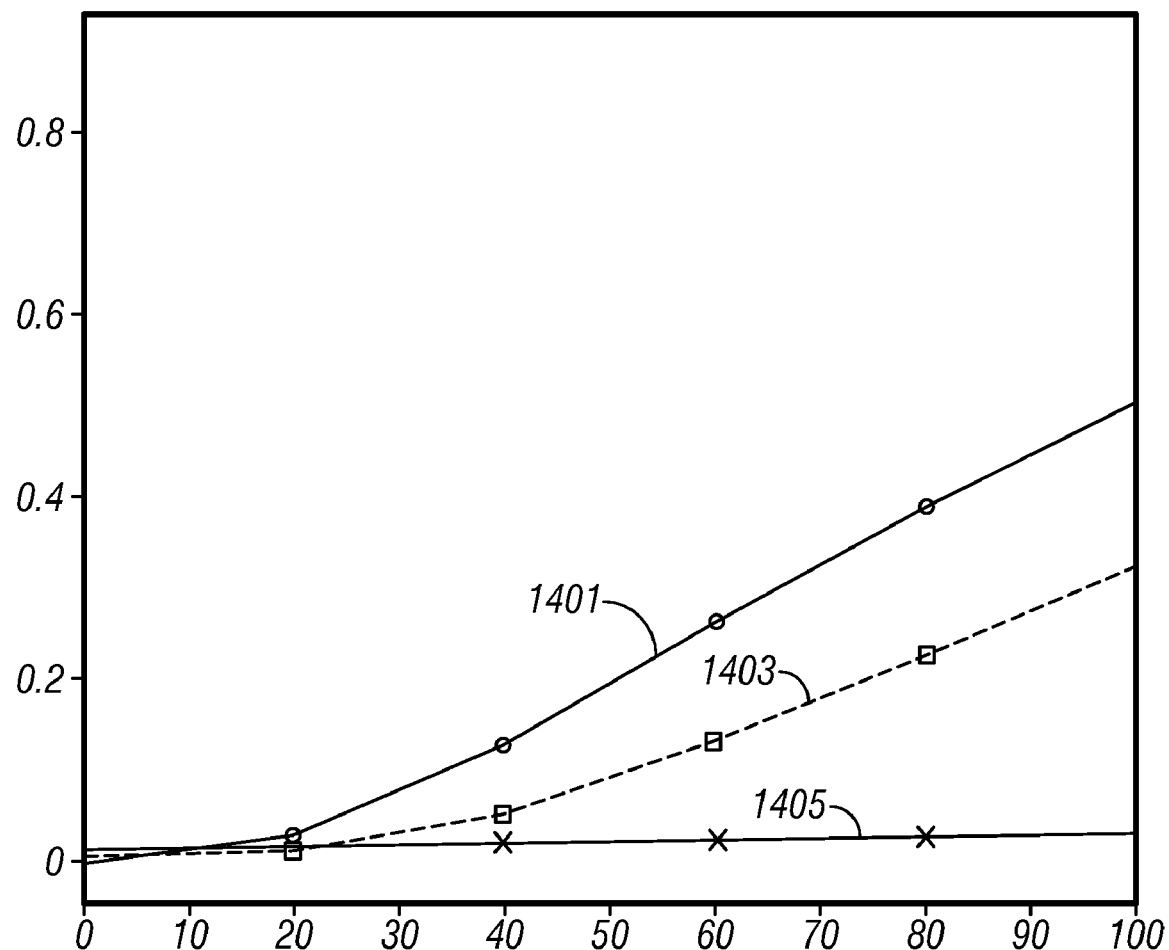
FIG. 14 shows a comparison of the efficiency of the different saturation methods.

Turning next to FIG. 14, a comparison is shown between the efficiencies of the simple rectangular pulse 1401, the variable frequency pulse 1405 of FIG. 9, and the stepped phase modulation, an approximation of quadrature phase modulation, 1403 of FIGS. 12A, 12B. The efficiency of the stepped-phase modulation 1403 in FIG. 14 is better than that of the rectangular pulse 1401 but worse than that of the tailored frequency sweep 1405. The efficiency of the stepped-phase modulation can be improved, though. This is possible by deviating from the simple quadratic phase change with the aim to get a frequency spectrum that is not "rectangular" like 1301 in FIG. 13 but rather has a shape more like 1001 in FIG. 10.

In view of the discussion above, the advantages of having an RF coil just for saturation purposes becomes clear. The RF coil for saturation purposes may be the same as or in addition to the RF coil that is used for transmitting and receiving signals. An advantage of having a saturation coil separate from the receive coil is that it is possible to have the saturation field stronger and more orthogonal to the static field.

Referring now to FIG. 16, the advantage of the structure of the "field forming" solenoid group is discussed. While not contemplated by Slade, a number of modifications may be made in view of the above disclosure. To address the problem due to the limited bandwidth of the transmit antenna we can use the plurality of transmit coils for the saturation pulses. Each antenna can be tuned to a different frequency. A further advantage is that these antenna(s) can be closer to the region where saturation is wanted; this improves at the same time the orthogonality between $B_1$ and $B_0$ fields, increasing the effectiveness of these saturation antenna(s) even more. In addition, the excitation of the transmit coils on the opposite sides of the center plane can be made asymmetric, so that saturated region is larger in the direction of tool motion than in the opposite direction. Using appropriate modeling techniques, it is also possible to dynamically alter the $B_1$ field based upon an average rate of penetration of the drillbit.

Figure 17:
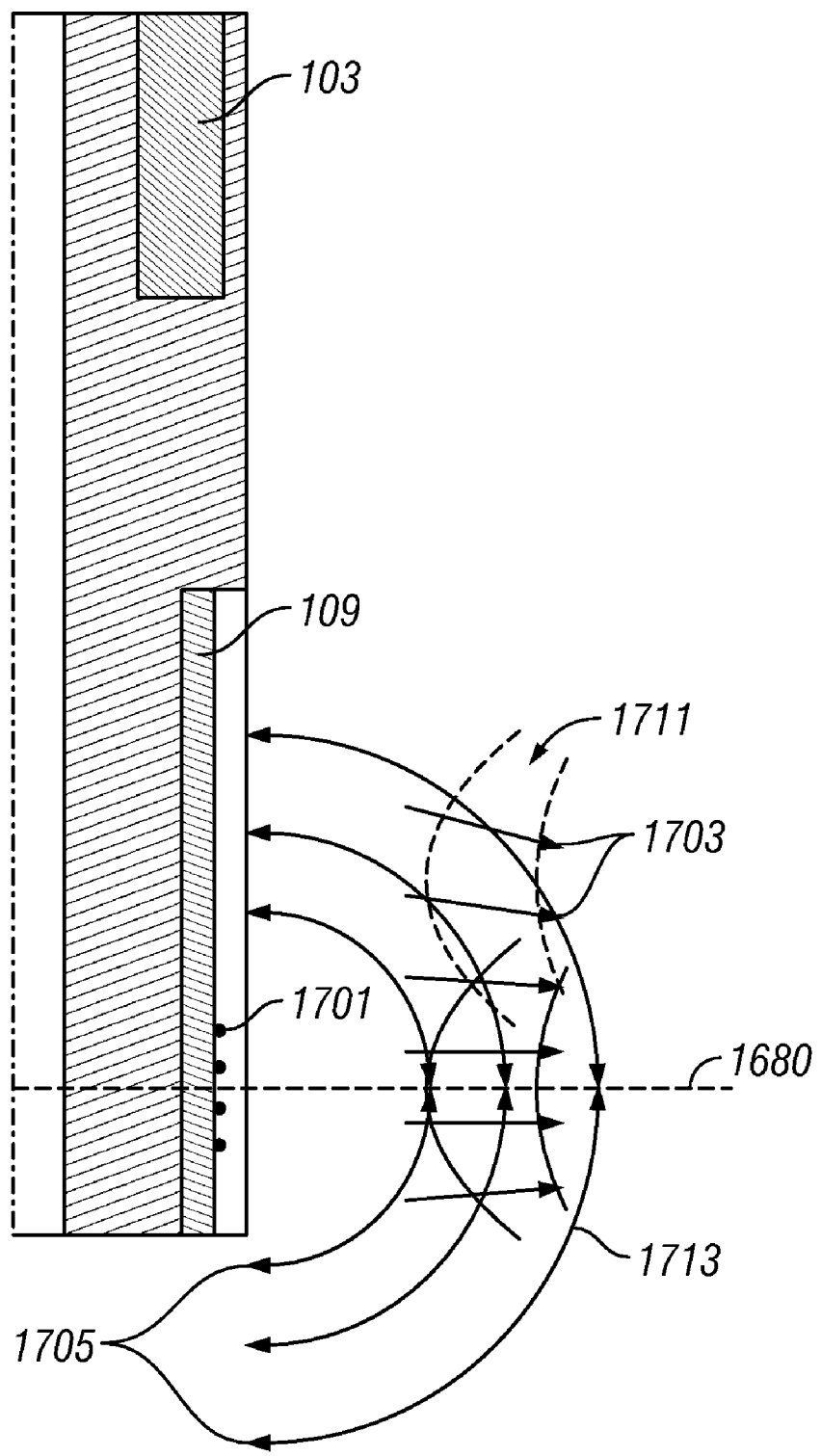
FIG. 17 shows the transmitting antenna coil and field configuration for another embodiment of the disclosure.

Turning now to FIG. 17, an NMR tool is shown with one of the permanent magnets 103, the center line 1680, the antenna core 109 and a transmit coil 1701. The $B_0$ field direction is given by the solid arrows 1703 and the RF field lines are given by the double arrows 1705. Also shown in the figure is the region between the dotted contour lines 1711 that needs to be saturated in order for a good NMR signal. With tool motion, this region will move into the region between the lines 1713. It can be seen that orthogonality is satisfied in region between the lines 1713 but is not satisfied in the region between the lines 1711 (the region for saturation).

Figure 18:
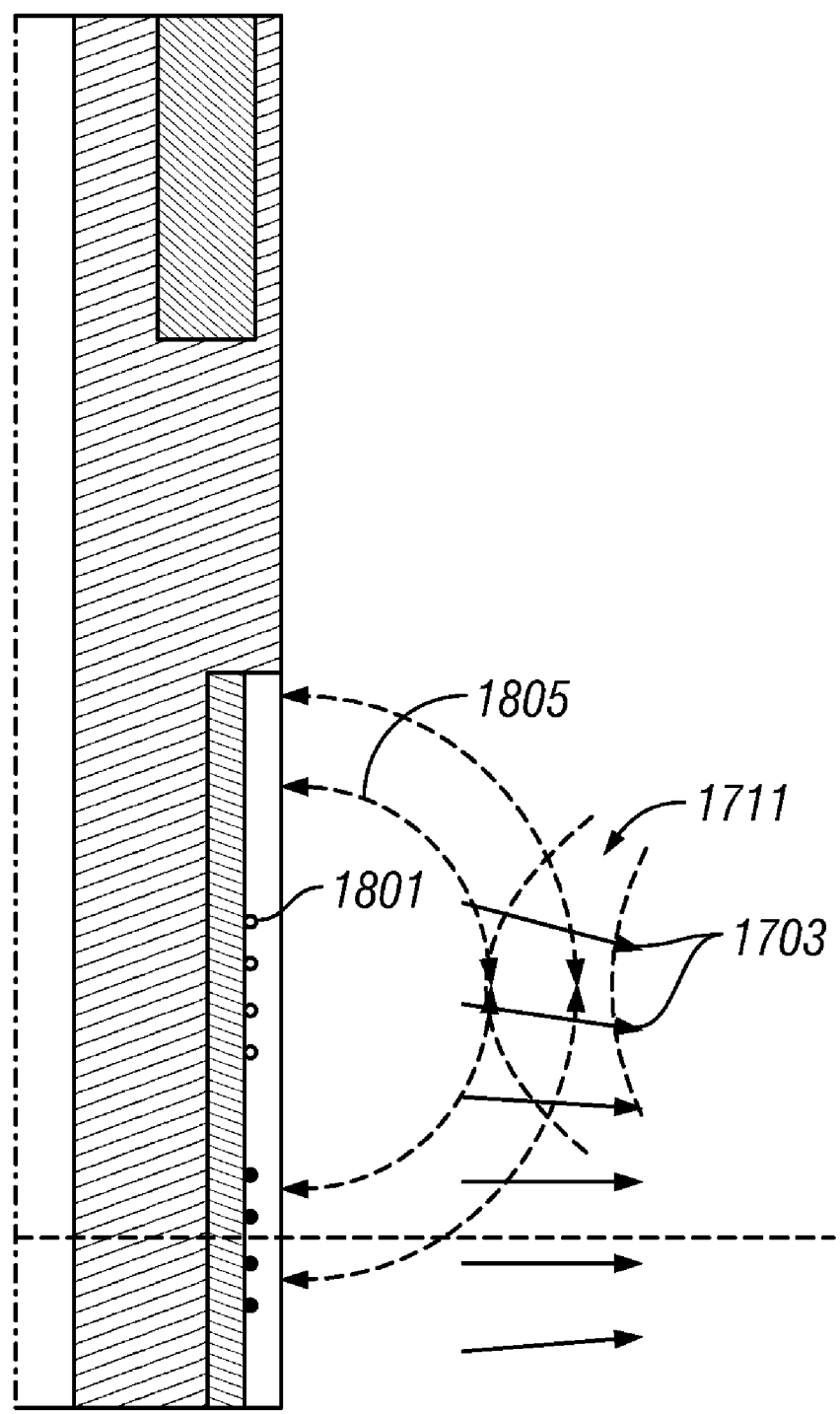
FIG. 18 shows the disposition of a saturating coil in the antenna arrangement of FIG. 17.

FIG. 18 shows, in addition to the tool of FIG. 17, a saturation coil 1801. There is now good orthgonality between the RF field lines 1805 of the saturation coil and the $B_0$ lines 1703.

Data acquired by the NMR logging tool may be used using known methods to determine formation properties such as porosity, a $T_2$ distribution, a $T_1$ distribution, and a permeability, and to record the determined formation properties on a suitable medium. As noted above, saturation using the methods disclosed herein is particularly useful when followed by a DTW for determination of $T_1$-affected $T_2$ distributions and fluid typing, and by a saturation recovery sequence for determination of $T_1$ distributions. These methods are not discussed here.

The disclosure has been described with reference to a NMR device that is part of a BHA conveyed on a drillstring. The disclosure is equally applicable for NMR devices conveyed on coiled tubing, wireline, and slickline as part of a logging string. Collectively, the logging string and the BHA may be referred to as a downhole assembly. The control described herein may be done using a downhole processor and the results stored on a suitable memory downhole or telemetered to the surface. Alternatively, the data may be stored on a downhole memory and processed when the BHA is tripped out of the borehole. With improved telemetry capability, it should be possible to telemeter the NMR measurements to a surface location and do the processing there.

Implicit in the processing of the data is the use of a computer program implemented on a suitable machine readable medium that enables the processor to perform the control and processing. The machine readable medium may include ROMs, EPROMs, EAROMs, Flash Memories and Optical disks.

While the foregoing disclosure is directed to the specific embodiments of the disclosure, various modifications will be apparent to those skilled in the art.

What is claimed is:

1. An apparatus for evaluating an earth formation, the apparatus comprising:
    a downhole assembly configured to be conveyed in a borehole;
    a magnet arrangement on a tool on the downhole assembly configured to generate a static magnetic field in the earth formation;
    at least one radio-frequency (RF) coil on the downhole assembly configured to generate an RF field in the earth formation; and
    a processor configured to:
        activate the at least one RF coil with at least one pulse sequence which substantially saturates nuclear spins in a region of the earth formation, and generates at least one signal from the region of substantial saturation of spins and generates substantially no signal from outside the region;
    wherein there is an axial movement of the tool between a start time of the at least one pulse sequence and an end time of the at least one pulse sequence; and
    wherein the processor is further configured to alter a frequency spectrum of at least one pulse in the at least one pulse sequence using a shape of the region and a static magnetic field $B_0$ in the region for a resonance condition.

2. The apparatus of claim 1 wherein the processor is further configured to: use the at least one signal to estimate at least one of: (I) a longitudinal relaxation time $T_1$ of the formation, (II) a transverse relaxation time $T_2$ of the formation, and (III) a fluid content of the formation.

3. The apparatus of claim 1 wherein the processor is further configured to alter the frequency spectrum of at least one pulse in the at least one pulse sequence by further using a component of the RF magnetic field $B_1$ that is substantially orthogonal to the static magnetic field $B_0$.

4. The apparatus of claim 1 wherein the at least one pulse sequence comprises an aperiodic pulse sequence.

5. The apparatus of claim 4 wherein the aperiodic pulse sequence further comprises pulses with phase selected from the group consisting of: (i) 0°, (ii) 90°, (iii) 180°, and (iv) 270°.

6. The apparatus of claim 1 wherein the processor is further configured to alter a frequency spectrum of at least one pulse of the at least one pulse sequence by at least one of: (i) a frequency modulation, (ii) a phase modulation, and (iii) stochastic pulsing.

7. The apparatus of claim 1 wherein the at least one RF coil further comprises a first RF coil configured to generate the at least one pulse sequence and a second RF coil configured to receive the at least one signal.

8. The apparatus of claim 1 wherein the at least one RF coil further comprises at least two RF coils, wherein a first RF coil substantially saturates the nuclear spins in the region and a second RF coil generates the at least one signal.

9. The apparatus of claim 1 wherein the downhole assembly is configured to be conveyed into the borehole on a conveyance device selected from: (i) a wireline, and (ii) a drilling tubular.

10. A method of evaluating an earth formation, the method comprising:
    conveying a downhole assembly in a borehole;
    using a magnet arrangement on a tool on the downhole assembly to generate a static magnetic field in a region of the earth formation;
    using at least one radio-frequency (RF) coil to generate an RF field in the region; and
    activating the at least one RF coil with at least one pulse sequence which substantially saturates nuclear spins in the region, and generates at least one signal from the region of substantial saturations of spins and generates substantially no signal from outside the region;

wherein there is an axial movement of the tool between a start time of the at least one pulse sequence and an end time of the at least one pulse sequence and wherein a frequency spectrum of at least one pulse in the at least one pulse sequence is altered using a shape of the region and a static magnetic field $B_0$ in the region for a resonance condition.

11. The method of claim 10 further comprising:
using the at least one signal to estimate at least one of: (I) a longitudinal relaxation time $T_1$ of the formation, (II) a transverse relaxation time $T_2$ of the formation, and (III) a fluid content of the formation.

12. The method of claim 10 further comprising altering the frequency spectrum of at least one pulse in the at least one pulse sequence by further using a component of the RF magnetic field $B_1$ that is substantially orthogonal to the static magnetic field $B_0$.

13. The method of claim 10 further comprising using for the at least one pulse sequence an aperiodic pulse sequence.

14. The method of claim 13 further comprising modulating the pulses of the aperiodic pulse sequence with a phase selected from the group consisting of: (i) 0°, (ii) 90°, (iii) 180°, and (iv) 270°.

15. The method of claim 10 further comprising altering a frequency spectrum of at least one pulse in the at least one pulse sequence by at least one of: (i) a frequency modulation, (ii) a phase modulation, and (iii) stochastic pulsing.

16. The method of claim 10 further comprising using a first RF coil to generate a second pulse sequence and a second RF coil to receiver the at least one signal.

17. The method of claim 10 further comprising using a first RF coil operated for substantially saturating the nuclear spins in the region and using a second RF coil for generating the at least one signal.

18. A computer-readable medium product having thereon instructions that when read by a processor cause the processor to execute a method, the method comprising:

determining a property of an earth formation selected from (I) a longitudinal relaxation time $T_1$ of the formation, (II) a transverse relaxation time $T_2$ of the formation, and (III) a fluid content of the formation using at least one signal from an earth formation acquired by a nuclear magnetic resonance (NMR) tool following application of:

(a) a static magnetic field in the earth formation during an axial motion of the NMR tool, (b) at least one radio frequency (RF) pulse sequence which substantially saturates nuclear spins in a region of the earth formation and generates the at least one signal from the region, wherein the at least one pulse sequence generates substantially no signal from outside the region wherein a frequency spectrum of at least one pulse in the at least one pulse sequence is altered using a shape of the region and a static magnetic field $B_0$ in the region of a resonance condition.

19. The medium of claim 18 further comprising at least one of: (i) ROM, (ii) and EPROM, (iii) an EAROM, (iv) a flash memory, and (v) an optical disk.

* * * * *